(12) United States Patent
Al-Dughaither et al.

(10) Patent No.: US 11,285,469 B2
(45) Date of Patent: Mar. 29, 2022

(54) METHOD FOR PREPARATION OF A CATALYST SOLUTION FOR SELECTIVE 1-HEXENE PRODUCTION

(71) Applicant: SABIC GLOBAL TECHNOLOGIES B.V., Bergen Op Zoom (NL)

(72) Inventors: Abdullah Saad Al-Dughaither, Riyadh (SA); Shahid Azam, Riyadh (SA); Abdulmajeed Mohammed Al-Hamdan, Riyadh (SA); Dafer Mubarak Alshahrani, Riyadh (SA); Sebastiano Licciulli, Riyadh (SA); Andreas Meiswinkel, Munich (SA); Heinz Bolt, Munich (DE); Wolfgang Muller, Munich (DE); Anina Wohl, Munich (DE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 440 days.

(21) Appl. No.: 16/473,674

(22) PCT Filed: Dec. 28, 2017

(86) PCT No.: PCT/IB2017/058473
§ 371 (c)(1),
(2) Date: Jun. 26, 2019

(87) PCT Pub. No.: WO2018/122773
PCT Pub. Date: Jul. 5, 2018

(65) Prior Publication Data
US 2019/0351403 A1    Nov. 21, 2019

Related U.S. Application Data

(60) Provisional application No. 62/440,554, filed on Dec. 30, 2016.

(51) Int. Cl.
*B01J 37/04* (2006.01)
*B01J 31/02* (2006.01)
(Continued)

(52) U.S. Cl.
CPC ........... *B01J 37/04* (2013.01); *B01J 31/0239* (2013.01); *B01J 31/0268* (2013.01);
(Continued)

(58) Field of Classification Search
CPC .... B01J 37/04; B01J 31/0239; B01J 31/0286; B01J 31/143; B01J 2231/20;
(Continued)

(56) References Cited

U.S. PATENT DOCUMENTS 4,024,170 A    5/1977    Atwood
4,768,384 A    9/1988    Flecken et al.
(Continued)

FOREIGN PATENT DOCUMENTS

CA    2249946 A1    4/2000
CN    105960417    9/2016
(Continued)

OTHER PUBLICATIONS

Fengkai et al.; "Chemical Production Technology"; Tianjin University Press; Aug. 2008; p. 80.
(Continued)

*Primary Examiner* — Ali Z Fadhel
(74) *Attorney, Agent, or Firm* — Norton Rose Fulbright US LLP

(57) ABSTRACT

A method for preparing a homogenous catalyst for use in preparing a linear alpha olefin includes: preparing a first pre-catalyst solution by mixing a chromium source and a ligand in a first solvent, wherein the first pre-catalyst solution is stored in a first vessel; preparing a second pre-catalyst solution by mixing an organoaluminum compound and a
(Continued)

modifier in a second solvent, wherein the second pre-catalyst solution is stored in a second vessel; and simultaneously feeding the first pre-catalyst solution and the second pre-catalyst solution directly into a reaction vessel, wherein the reaction vessel includes a third solvent.

17 Claims, 1 Drawing Sheet

(51) Int. Cl.
    *B01J 31/14*     (2006.01)
    *C07C 11/107*     (2006.01)

(52) U.S. Cl.
    CPC ............ *B01J 31/143* (2013.01); *C07C 11/107* (2013.01); *B01J 2231/20* (2013.01); *B01J 2531/62* (2013.01); *C07C 2531/14* (2013.01); *C07C 2531/18* (2013.01); *C07C 2531/34* (2013.01)

(58) Field of Classification Search
    CPC .... B01J 2531/62; B01J 31/187; B01J 31/188; B01J 23/26; B01J 31/1845; C07C 11/107; C07C 2531/14; C07C 2531/18; C07C 2531/34; C07C 2/32
    See application file for complete search history.

(56) References Cited

U.S. PATENT DOCUMENTS

| | | | |
|---|---|---|---|
| 5,550,306 | A | 8/1996 | Chauvin et al. |
| 5,670,682 | A | 9/1997 | Sangokoya |
| 6,096,680 | A | 8/2000 | Park |
| 6,133,495 | A | 10/2000 | Urata et al. |
| 6,706,657 | B2 | 3/2004 | Commereuc et al. |
| 7,291,575 | B2 | 11/2007 | Shih |
| 7,799,882 | B2 | 9/2010 | Jiang et al. |
| 8,907,032 | B2 | 12/2014 | Kol et al. |
| 2003/0199649 | A1 | 10/2003 | Orbison et al. |
| 2007/0129583 | A1 | 6/2007 | Deboer et al. |
| 2008/0022658 | A1 | 1/2008 | Viola et al. |
| 2010/0267904 | A1 | 10/2010 | Fouarge |
| 2014/0005034 | A1* | 1/2014 | Wohl ............. C08F 4/78 502/108 |
| 2017/0165657 | A1* | 6/2017 | Khurram ............ B01J 31/0268 |

FOREIGN PATENT DOCUMENTS

| | | |
|---|---|---|
| EP | 1136122 A1 | 9/2001 |
| EP | 1578531 B1 | 8/2010 |
| EP | 2489431 A1 | 8/2012 |
| JP | H07163885 A | 6/1995 |
| JP | 2002233764 A | 8/2002 |
| JP | 2005513115 A | 5/2005 |
| RU | 2315658 | 1/2008 |
| RU | 2593375 | 8/2016 |
| WO | 8102422 A1 | 9/1981 |
| WO | WO 2007/057455 | 5/2007 |
| WO | 2009006979 A2 | 1/2009 |
| WO | 2009068157 A1 | 6/2009 |
| WO | 2009121456 A1 | 10/2009 |
| WO | 2010115520 A1 | 10/2010 |
| WO | 2015114611 A1 | 8/2015 |
| WO | 2018122703 A1 | 5/2018 |

OTHER PUBLICATIONS

Ning; "Advanced Inorganic Synthesis"; East China University of Science and Technology Press; Sep. 2007 p. 28.
Office Action issued in counterpart Russian Patent Application No. 2019119456, dated Feb. 20, 2020. (English Translation Provided).
Office Action issued in counterpart Russian Patent Application No. 2019119456, dated Nov. 12, 2020. (English Translation Provided).
International Search Report; International Application No. PCT/IB2017/058473; International Filing Date Dec. 28, 2017; dated Apr. 24, 2018, 5 pages.
Written Opinion of the International Searching Authority; International Application No. PCT/IB2017/058473; International Filing Date Dec. 28, 2017; dated Apr. 24, 2018, 6 pages.
Aluri et al.; "Coordination chemistry of new selective ethylene trimerisation ligand Ph2PN(iPr)P(Ph)NH(R) (R=iPr, Et) and tests in catalysis"; Dalton Trans., 2010, vol. 39, pp. 7911-7920.
Aluri et al.; "Synthesis, Coordination Chemistry, and Catalysis of the First 1,2-Bis(diphenylphosphino)-1,2-diphenylhydrazine, Ph2PN(Ph)N(Ph)PPh2" Organometallics 2010, vol. 29, pp. 226-231.
Atwood et al.; "Solid state structure and solution behavior of compounds of the type M[A12(CH3)6X]"; J. Organomental. Chem., 1972, vol. 42, pp. C77-C79.
Barden et al.; "A NMR Method to Probe the Nature of Liquid Clathrates"; Journal of inclusion Phenomena 1986, vol. 4, pp. 429-431.
Broome et al.; "The Solubilities of Dodecylammonium Chloride and its N-Methyl Derivatives in n-Hexane, Benzene and 95.0% Ethanol"; Journal of American Chemical Science; vol. 72, No. 7; 1950; pp. 3257-3260.
European Search Report for Application No. 11154663; Date of Completion of the Search: May 19, 2011, 3 pages.
Gaudet et al.; "Ternary Hydrogen Halide/Base/Benzene Mixtures: A New Generation of Liquid Clathrates"; Journal of Inclusion Phenomena 1988, vol. 6, pp. 425-428.
Hoibrey et al.; "Liquid clathrate formation in ionic liquid-aromatic mixtures"; Chem. Commun. 2003, pp. 476-477.
Hrncir et al.; "Indium-Based Liquid Clathrates III. Inclusion Compounds Derived from [Bu4N][InCl3X] Salts and Their Suitability as a Catalysis Medium"; Journal of Inclusion Phenomena 1988, vol. 6, pp. 233-236.
International Search Report; International Application No. PCT/EP2012/000092; International Filing Date: Jan. 11, 2012; dated Mar. 8, 2012; 5 Pages.
International Search Report; International Application No. PCT/IB2015/050826; dated May 15, 2015, 5 pages.
International Search Report; International Application No. PCT/IB2017/058301; International Filing Date; Dec. 21, 2017; dated Mar. 15, 2018, 5 pages.
Japanese Patent No. 2002233764; Date of Publication: Aug. 20, 2002; Abstract Only, 1 page.
Japanese Patent No. 2005513115; Date of Publication: May 12, 2005; Abstract Only, 2 pages.
Japanese Patent No. H07163885; Date of Publication: Jun. 27, 1995; Abstract Only; 2 pages.
Jerry L. Atwood; "New Inclusion Methods for Separations Problems" Separation Science and Technology 1984-85, vol. 19, pp. 751-759.
Luo Hongwei, Top Ten Chemical Engineering Chemical Industry Code of Practice and National Occupation Standards; China Knowledge Press, 2006, Machine Translation, 5 pages.
Martell et al.; "Synthesis and Structure of Mixed Chloride-Tetrachloroaluminate Salts": J. Chem. Soc. Dalton Trans. 1991, pp. 1495-1498.
Muller et al.; "A Kinetic Model for Selective Ethene Trimerization to 1-Hexene by a Novel Chromium Catalyst System" ChemCatChem 2010, vol. 2, pp. 1130-1142.
Peitz et al.; "A Selective Chromium Catalyst System for the Trimerization of Ethene and Its Coordination Chemistry" Eng. J. Inorg. Chem; 2010; pp. 1167-1171.
Peitz et al.; "Activation and Deactivation by Temperature: Behavior of Ph2PN(iPr)P(Ph)N(iPr)H in the Presence of Alkylaluminum Compounds Relevant to Catalytic Selective Ethene Trimerization"; Chem. Eur. J. 2010, vol. 16, pp. 12127-12132.
Peitz et al.; "An Alternative Mechanistic Concept for Homogeneous Selective Ethylene Oligomerization of Chromium-Based Catalysts: Binuclear Metallacycles as a Reason for 1-Octene Selectivity?"; Chem. Eur. J. 2010, vol. 16, pp. 7670-7676.

(56) References Cited

OTHER PUBLICATIONS

Peitz et al.; "Metalation and Transmetalation Studies on Ph2PN(iPr)P(Ph)N(iPr)H for Selective Ethene Trimerization to 1-Hexene"; Organometallics 2010, vol. 29, pp. 5263-5268.
Peitz et al.; Abstracts of Papers, 240th ACS National Meeting, Boston, MA, United States, Aug. 22-26, 2010 (2010), INOR-655.
Peulecke et al.; "Immobilized Chromium Catalyst System for Selective Ethene Trimerization to 1-Hexene with a PNPNH Ligand"; ChemCatChem 2010, vol. 2, pp. 1079-1081.
Sangokoya et al.; "Optically Active Organoaluminum Based Inclusion Compounds: Synthesis and Characterization of (S)-(−)x-[(C6H5)CH(CH3)N(CH3)3][Al2R6I]R=CH3, CH2H5)"; Journal of Inclusion Phenomena; vol. 6; 1988 pp. 263-266.
Wohl et al.; "Influence of Process Parameters on the Reaction Kinetics of the Chromium-Catalyzed Trimerization of Ethylene"; Chem. Eur. J. 2010, vol. 16, pp. 7833-7842.
Written Opinion of the International Search Report; International Application No. PCT/IB2015/050826; dated May 15, 2015, 6 pages.
Written Opinion of the International Searching Authority; International Application No. PCT/EP2012/000092; International Filing Date: Jan. 11, 2012; dated Mar. 8, 2012; 4 Pages.
Written Opinion of the International Searching Authority; International Application No. PCT/IB2017/058301; International Filing Date Dec. 21, 2017; dated Mar. 15, 2018, 5 pages.
Office Action issued in Corresponding Chinese Application No. 201780081687.8, dated Nov. 19, 2021 (No English Translation provided).

\* cited by examiner

METHOD FOR PREPARATION OF A CATALYST SOLUTION FOR SELECTIVE 1-HEXENE PRODUCTION

CROSS REFERENCE TO RELATED APPLICATIONS

This application is a National Stage Application of PCT/IB2017/058473, filed Dec. 28, 2017, which claims the benefit of U.S. Provisional Application No. 62/440,554, filed Dec. 30, 2016, both of which are incorporated by reference in their entirety herein.

BACKGROUND

Linear alpha olefins (LAOs) are olefins with a chemical formula $C_xH_{2x}$, distinguished from other mono-olefins with a similar molecular formula by linearity of the hydrocarbon chain and the position of the double bond at the primary or alpha position. Linear alpha olefins comprise a class of industrially important alpha-olefins, including 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ olefins. Linear alpha-olefins (LAOs), for example those with four to 30 carbon atoms, are compounds which are, for example, widely used and required in large quantities as comonomers for modifying the properties of polyolefins or as a starting material for the production of plasticizers, household cleansers, flotation agents, emulsifiers, drinking fluids, surface-active substances, synthetic oils, putties, sealants, and the like. Existing processes for the production of linear alpha olefins typically rely on the oligomerization of ethylene.

Methods for the oligomerization of ethylene using various catalyst compositions are known. Typically, if very unspecific catalysts are used, a broad product distribution is obtained from C4 to higher olefins and even polymeric materials. Recently, catalyst compositions for the oligomerization of ethylene have been developed which are more specific to, for example, trimerization or tetramerization, thus resulting in a narrower product distribution, but still also producing higher linear alpha-olefins and polymeric materials. Catalyst systems and processes for the oligomerization of ethylene, in particular for the selective trimerization of ethylene to 1-hexene and/or the tetramerization to 1-octene are widely known.

The selective ethylene trimerization catalysts disclosed so far in scientific and patent literature generally have to cope with the following challenges: very narrow or unsuitable window of operability of the catalyst system in terms of process conditions such as temperature, pressure, residence time, catalyst concentration, and the like.

Selective 1-Hexene production via on-purpose linear alpha olefin technology utilizes a homogenous catalyst formed of four components. Previous catalyst compositions comprising, for example, a chromium compound, a ligand, a modifier and an activator show several disadvantages. First, some of the catalyst's components are poorly soluble in the aromatic solvents of the process. This is especially true for the modifier. Second, all catalyst constituents need to be meticulously metered into the reactor to adjust the productivity very precisely and avoid thermal runaways. This prohibits the use of slurry systems or any system for handling solids. Instead, the catalyst components should be introduced into the reactor by dosing pumps. Third, for high productivities and high selectivity, the catalyst composition needs to be precisely defined in terms of total chromium concentration and particularly regarding the molar ratios of ligand/chromium, aluminum/chromium and modifier/chromium. Fourth, preparation of the entire homogenous catalyst, including all four components, is not feasible in a technical environment due to the degradation of the catalyst on a timescale of equal or greater than approximately one day. This degradation results in deteriorating activity and increased wax/polymer formation. Further, ingress of moisture or air from the environment into the storage equipment during unloading of catalyst components should be prevented. The catalyst components are mixed and then immediately transferred to the oligomerization reactor to avoid decomposition of the catalyst system leading to deteriorating activities and side product formation.

Due to the catalyst's short shelf life, it is necessary to prepare the homogenous catalyst directly before injection into reactors with minimum transportation time. The preparation of the homogenous catalyst must assure base line catalyst activity in the reactor.

Thus, there is a need for a method of preparing a homogenous catalyst that assures baseline catalyst activity in a reactor and to provide a process for preparing a catalyst composition for oligomerization of ethylene to overcome the problems associated with the catalyst's short shelf life as described herein and create a new method of creating a usable homogenous catalyst.

SUMMARY

Disclosed, in various embodiments, is a method of preparing a homogenous catalyst for the production of linear alpha olefins.

A method for preparing a homogenous catalyst for use in preparing a linear alpha olefin comprises: preparing a first pre-catalyst solution by mixing a chromium source and a ligand in a first solvent, wherein the first pre-catalyst solution is stored in a first vessel; preparing a second pre-catalyst solution by mixing an organoaluminum compound and a modifier in a second solvent, wherein the second pre-catalyst solution is stored in a second vessel; and simultaneously feeding the first pre-catalyst solution and the second pre-catalyst solution directly into a reaction vessel, wherein the reaction vessel includes a third solvent.

A method for preparing a homogenous catalyst for use in preparing a linear alpha olefin comprises: preparing a first pre-catalyst solution by mixing a chromium source and a ligand in a first solvent, wherein the first pre-catalyst solution is stored in a first vessel; preparing a second pre-catalyst solution by mixing an organoaluminum compound and a modifier in a second solvent, wherein the second pre-catalyst is stored in a second vessel; and simultaneously feeding the first pre-catalyst solution and the second pre-catalyst solution directly into a hydrocarbon solvent feed upstream from the reaction vessel.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
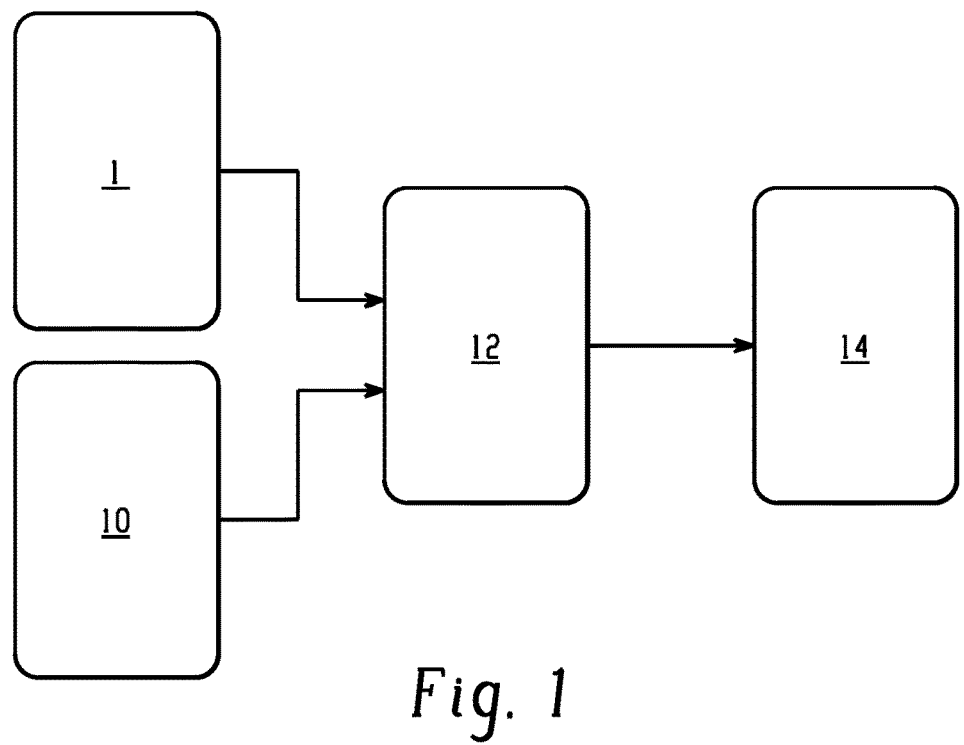
FIG. 1 is a block flow diagram for catalyst preparation and dosing.

Disclosed herein is a method that is able to overcome the problem of short catalyst shelf life by preparing a homogenous catalyst for use in on-purpose linear alpha olefin technology in a two-step process. Accordingly, described herein is a system and method of preparing catalyst compositions for the oligomerization of ethylene to produce 1-hexene that results in catalyst compositions with a longer useful life (i.e., a longer shelf life). In the method, a first pre-catalyst solution and a second pre-catalyst solution are not premixed in a separate mixing vessel before being added to an oligomerization reactor. Instead, it was surprisingly discovered that the first pre-catalyst solution and the second pre-catalyst solution can be separately and directly fend into an oligomerization reactor or even into a solvent feed line of such a reactor in order to ensure sufficient premixing of the solutions by using the velocity of the solvent feed line.

The method for preparation of a homogenous catalyst can employ three solid components and a liquid component in a two-step process. The homogenous catalyst composition can include, for example, (i) a chromium source, (ii) a ligand, (iii) a modifier, (iv) a solvent, and (v) an organoaluminum compound. The first step can include preparation of two pre-catalyst solutions. The first pre-catalyst solution can comprise a chromium source and a ligand in a first solvent. The second pre-catalyst solution can include an organoaluminum compound and a modifier in a second solvent. The second step can include simultaneously injecting the pre-catalyst solutions separately into hydrocarbon feed streams upstream of the reactor, or simultaneously injecting the pre-catalyst solutions directly into the reactor.

1-Hexene is commonly manufactured by two general routes: (i) full-range processes via the oligomerization of ethylene and (ii) on-purpose technology. A minor route to 1-hexene, used commercially on smaller scales, is the dehydration of hexanol. Prior to the 1970s, 1-hexene was also manufactured by the thermal cracking of waxes. Linear internal hexenes were manufactured by chlorination/dehydrochlorination of linear paraffins.

"Ethylene oligomerization" combines ethylene molecules to produce linear alpha-olefins of various chain lengths with an even number of carbon atoms. This approach results in a distribution of alpha-olefins. Oligomerization of ethylene can produce 1-hexene.

Fischer-Tropsch synthesis to make fuels from synthesis gas derived from coal can recover 1-hexene from the aforementioned fuel streams, where the initial 1-hexene concentration cut can be 60% in a narrow distillation, with the remainder being vinylidenes, linear and branched internal olefins, linear and branched paraffins, alcohols, aldehydes, carboxylic acids, and aromatic compounds. The trimerization of ethylene by homogeneous catalysts has been demonstrated.

There are a wide range of applications for linear alpha olefins. The lower carbon numbers, 1-butene, 1-hexene and 1-octene can be used as comonomers in the production of polyethylene. High density polyethylene (HDPE) and linear low density polyethylene (LLDPE) can use approximately 2-4% and 8-10% of comonomers, respectively.

Another use of $C_4$-$C_8$ linear alpha olefins can be for production of linear aldehyde via oxo synthesis (hydroformylation) for later production of short-chain fatty acid, a carboxylic acid, by oxidation of an intermediate aldehyde, or linear alcohols for plasticizer application by hydrogenation of the aldehyde.

An application of 1-decene is in making polyalphaolefin synthetic lubricant base stock (PAO) and to make surfactants in a blend with higher linear alpha olefins.

$C_{10}$-$C_{14}$ linear alpha olefins can be used in making surfactants for aqueous detergent formulations. These carbon numbers can be reacted with benzene to make linear alkyl benzene (LAB), which can be further sulfonated to linear alkyl benzene sulfonate (LABS), a popular relatively low cost surfactant for household and industrial detergent applications.

Although some $C_{14}$ alpha olefin can be sold into aqueous detergent applications, $C_{14}$ has other applications such as being converted into chloroparaffins. A recent application of $C_{14}$ is as on-land drilling fluid base stock, replacing diesel or kerosene in that application. Although $C_{14}$ is more expensive than middle distillates, it has a significant advantage environmentally, being much more biodegradable, and in handling the material, being much less irritating to skin and less toxic.

$C_{16}$-$C_{18}$ linear olefins find their primary application as the hydrophobes in oil-soluble surfactants and as lubricating fluids themselves. $C_{16}$-$C_{18}$ alpha or internal olefins are used as synthetic drilling fluid base for high value, primarily off-shore synthetic drilling fluids. The preferred materials for the synthetic drilling fluid application are linear internal olefins, which are primarily made by isomerizing linear alpha-olefins to an internal position. The higher internal olefins appear to form a more lubricious layer at the metal surface and are recognized as a better lubricant. Another application for $C_{16}$-$C_{18}$ olefins is in paper sizing. Linear alpha olefins are, once again, isomerized into linear internal olefins are then reacted with maleic anhydride to make an alkyl succinic anhydride (ASA), a popular paper sizing chemical.

$C_{20}$-$C_{30}$ linear alpha olefins production capacity can be 5-10% of the total production of a linear alpha olefin plant. These are used in a number of reactive and non-reactive applications, including as feedstocks to make heavy linear alkyl benzene (LAB) and low molecular weight polymers used to enhance properties of waxes.

The use of 1-hexene can be as a comonomer in production of polyethylene. High-density polyethylene (HDPE) and linear low-density polyethylene (LLDPE) use approximately 2-4% and 8-10% of comonomers, respectively.

Another use of 1-hexene is the production of the linear aldehyde heptanal via hydroformylation (oxo synthesis). Heptanal can be converted to the short-chain fatty acid heptanoic acid or the alcohol heptanol.

A more complete understanding of the components, processes, and apparatuses disclosed herein can be obtained by reference to the accompanying drawings. These figures (also referred herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 2:
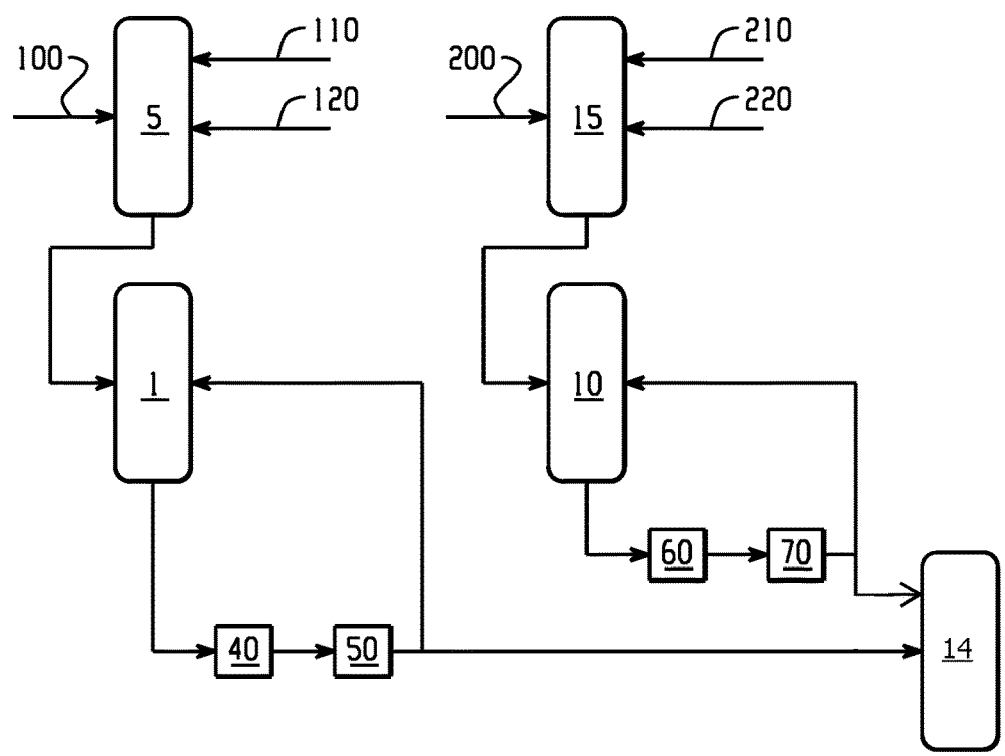
FIG. 2 is a schematic representation of a catalyst preformation unit.

Turning now to FIG. 1 and FIG. 2, the pre-catalyst solutions can each be prepared in separate reaction vessels 1, 10 equipped with continuous agitation/mixing to ensure homogenous mixing of catalyst components with a solvent, e.g., a hydrocarbon solvent. During preparation and storage of the pre-catalyst solutions, blanketing with an inert gas can be used to avoid ingress of moisture or air from the environment into the equipment.

The first pre-catalyst solution can be prepared separately, for example, batch-wise or in continuous mode, and then stored in a first vessel 1 at a temperature below the melting points of each component of the first pre-catalyst solution. The first pre-catalyst solution can include a first component 110, for example a chromium source, and a second component 120, for example, a ligand, which can be mixed when added to a solid catalyst preparation unit 5. The first pre-catalyst solution can further include a first solvent 100. The first solvent 100 can be an aromatic or aliphatic solvent, or a combination comprising at least one of the foregoing. For example, the first solvent can be toluene, benzene, ethylbenzene, cumenene, xylene, mesitylene, hexane, octane, cyclohexane, olefins, such as hexene, heptane, octene, or ethers, such as diethylether or tetrahydrofurane. In an embodiment, the solvent can be an aromatic solvent.

The solid catalyst preparation unit 5 can be in fluid connection with a first vessel 1, for example the solid catalyst preparation unit 5 can be connected to the first vessel 1 with piping. The first pre-catalyst solution can flow from the solid catalyst preparation unit 5 to the first vessel 1. The first pre-catalyst solution can then be stored in the first vessel 1 for 1 hour to 90 days, for example, 1 hour to 7 days, for example 1 to 72 hours. The first pre-catalyst solution can be circulated through a first pump 40 and a first cooler 50 and returned to the first vessel 1 wherein the first pre-catalyst solution can be maintained at a temperature of 0-50° C., for example, a temperature of 10-40° C., for example, 15-35° C. to sustain catalyst activity. The first pre-catalyst solution can be maintained at a pressure of 30 kiloPascals to 8000 kiloPascals, for example, 50 kiloPascals to 6000 kiloPascals, for example, 50 kiloPascals to 3500 kiloPascals within the first vessel 1.

The second pre-catalyst solution can be prepared separately, for example, batch-wise or in continuous mode, and then stored in a second vessel 10. The second pre-catalyst solution can include a third catalyst component 210, for example an organoaluminum compound and a fourth catalyst component 220, for example a modifier in a second solvent 200. Heat generated from the combination of the organoaluminum compound with the modifier from the reaction vessel can be removed from the reaction vessel 14. The second solvent 200 can be an aromatic or aliphatic solvent, or a combination comprising at least one of the foregoing. For example, the first solvent can be toluene, benzene, ethylbenzene, cumenene, xylene, mesitylene, hexane, octane, cyclohexane, olefins, such as hexene, heptane, octene, or ethers, such as diethylether or tetrahydrofurane. In an embodiment, the solvent can be an aromatic solvent. The second pre-catalyst solution can be stored in the second vessel 10 for 1 hour to 90 days, for example, 1 hour to 7 days, for example 1 to 72 hours. The second pre-catalyst solution can be circulated through a second pump 60 and a second cooler 70 and returned to the second vessel 10 wherein the second pre-catalyst solution can be maintained at a temperature of 0-50° C., for example, a temperature of 10-40° C., for example, 15-35° C. to sustain catalyst activity. The second pre-catalyst solution can be maintained at a pressure of 30 kiloPascals to 8000 kiloPascals, for example, 50 kiloPascals to 6000 kiloPascals, for example, 50 kiloPascals to 3500 kiloPascals within the second vessel 10.

After preparation, the first and second pre-catalyst solutions can be stored separately in a first vessel 1, and a second vessel 10, respectively, for further use in the process. The recirculation of the pre-catalyst solutions separately through pumps 40, 60 and coolers 50, 70, can assist in cooling and maintaining homogeneity of the stored pre-catalyst solutions.

The first pre-catalyst solution and the second pre-catalyst solution can be injected directly into a reaction vessel 14, e.g., a linear alpha olefin reactor 14. In another aspect, the first and second pre-catalyst solutions can be directly injected into one or more separate hydrocarbon feed streams upstream of the reactor for better distribution inside of the reaction vessel 14.

The accuracy and precision of dosed catalyst quantities can be ensured by proper design of conventional solid and liquid feeding systems. The pre-catalyst solutions can be injected into the reactor at a pre-defined ratio. For example, the ratio of the first pre-catalyst solution to the second pre-catalyst solution can be 1:1, but a wider range is possible depending on the concentration of the stock solutions. For example, a molar ratio of the ligand/Cr is 0.5 to 50, for example, 0.8 to 2.0. A molar ratio of Al/Cr can be 1.0 to 1000, for example, 10 to 100. A molar ratio of the modifier/Cr can be 0.1 to 100, for example, 1 to 20. The residence time of the catalyst from the point where the two pre-catalyst solutions are created until injected into the reactor can be based upon the catalyst shelf life, appropriate selection of pipe design and layout. The dosing of the pre-catalyst solutions into the reactor 14 can be flow-controlled.

Turning now to the catalyst, the various components of the catalyst are described in more detail.

(i) Chromium Compound

The chromium compound can be an organic salt, an inorganic salt, a coordination complex, or an organometallic complex of Cr(II) or Cr(III). In one embodiment, the chromium compound is an organometallic complex, preferably of Cr(II) or Cr(III). Examples of the chromium compounds include $CrCl_3(tetrahydrofuran)_3$, Cr(III)acetyl acetonate, Cr(III)octanoate, Cr(III)-2-ethylhexanoate, chromium hexacarbonyl, Cr(III)chloride, benzene(tricarbonyl)-chromium. A combination comprising at least one of the foregoing chromium compounds can be used.

The concentration of the chromium compound can vary depending on the particular compound used and the desired reaction rate. In some embodiments the concentration of the chromium compound is from about 0.01 to about 100 millimole per liter (mmol/l), about 0.01 to about 10 mmol/l, about 0.01 to about 1 mmol/l, about 0.1 to about 100 mmol/l, about 0.1 to about 10 mmol/l, about 0.1 to about 1.0 mmol/l, about 1 to about 10 mmol/l, and about 1 to about 100 mmol/l. Preferably, the concentration of the chromium compound is from about 0.1 to about 1.0 mmol/l, most preferably, about 0.5 to about 0.6 mmol/L.

(ii) Ligand

The ligand can be a PNPNH ligand. The ligand can have the backbone PNPNH, which as used herein has the general structure $R^1R^2P\text{---}N(R^3)\text{---}P(R^4)\text{---}N(R^5)\text{---}H$ wherein each of $R^1$, $R^2$, $R^3$, $R^4$, and $R^5$ is independently a hydrogen, halogen, $C_{1-18}$ hydrocarbyl group, amino group of the formula $NR^aR^b$ wherein each of $R^a$ and $R^b$ is independently hydrogen or a $C_{1-18}$ hydrocarbyl group, a silyl group of the formula $SiR^aR^bR^c$ wherein each of $R^a$, $R^b$, and $R^c$ is independently hydrogen or a $C_{1-18}$ hydrocarbyl group, or two of $R^1$, $R^2$, $R^3$, $R^4$, $R^5$, $R^a$, or $R^b$ taken together are a substituted or unsubstituted $C_{1-10}$ hydrocarbylene group linked to the same or different heteroatoms to form a heterocyclic structure. Exemplary ligands having a heterocyclic structure include the following

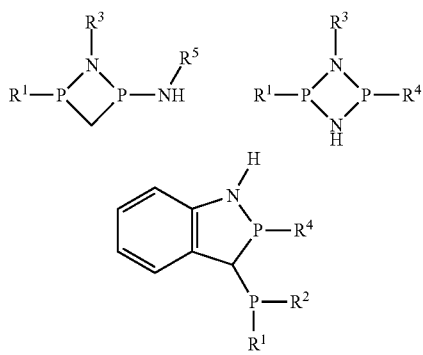

wherein $R^1$, $R^2$, $R^3$, $R^4$, $R^5$ are as described above. In a specific embodiment, each $R^1$, $R^2$, $R^3$, $R^4$, $R^5$ are independently hydrogen, substituted or unsubstituted $C_1$-$C_8$ alkyl, substituted or unsubstituted $C_6$-$C_{20}$ aryl, more preferably unsubstituted $C_1$-$C_6$ alkyl or unsubstituted $C_6$-$C_{10}$ aryl. A specific example of the ligand is (phenyl)$_2$PN(iso-propyl)P (phenyl)N(iso-propyl)H, commonly abbreviated Ph$_2$PN(i-Pr)P(Ph)NH(i-Pr). The ligand used herein has the general structure $R_1R_2P-N(R_3)-P(R_4)-N(R_5)-H$, wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, aryl and substituted aryl. The ligand can be, for example, Ph$_2$PN(iPr)P(Ph)N(iPr)H.

The molar ratio of ligand/Cr can be 0.5 to 50, 0.5 to 5, 0.8 to 2.0, 1.0 to 5.0, or 1.0 to 1.5.

(iii) Modifier

The modifier can be selected from ethers, anhydrides, amines, amides, quaternary ammonium salts, silicates, silyl ethers, siloxanes, esters, carbonates, ureas, carbamates, sulfoxides, sulfones, phosphoramides, silanes, acetals, or a combination comprising at least one of the foregoing. For example, the modifier can be selected from ammonium or phosphonium salts of the type [M$_4$E]X, [H$_3$ER]X, [H$_2$ER$_2$] X, [HER$_3$]X or [ER$_4$]X or_HX or RX with E=N or P, X=Cl, Br or I and R=alkyl, cycloalkyl, acyl, aryl, alkenyl, alkynyl or the corresponding bridging di-, tri- or multiunits, or ammonium or phosphonium salts based on cyclic amines, or a combination comprising at least one of the foregoing. The modifier can be present in a concentration amount of 0.1 to 15 mmol/L, for example, 0.3 to 0.5 mmol/L.

(iv) Solvents

The solvent, e.g., the first solvent, the second solvent or the third solvent can comprise an aromatic or aliphatic solvent, or a combination comprising at least one of the foregoing. For example, the first solvent can be toluene, benzene, ethylbenzene, cumenene, xylene, mesitylene, hexane, octane, cyclohexane, olefins, such as hexene, heptane, octene, or ethers, such as diethylether or tetrahydrofurane. In an embodiment, the solvent can be an aromatic solvent, for example, toluene.

(v) Organoaluminum Compound

The organoaluminum compound can be methylaluminoxane (MAO), modified methylaluminoxane (MMAO), ethylaluminum sesquichloride (EASC), diethylaluminum chloride (DEAC), trialkylaluminum, e.g., trimethylaluminum or triethylaluminum, isobutylealuminoxane (IBAO), tri-isobutyl aluminum (TIBA). A combination comprising at least one of the foregoing chromium compounds can be used. The organoaluminum compound can be present in a concentration amount of 0.24 to 2400 mmol/L, for example, 6 to 8 mmol/L.

The homogenous catalyst composition disclosed herein can be used in a process for the oligomerization of ethylene. Those skilled in the art will understand that oligomerization of ethylene to produce 1-hexene can be by trimerization of ethylene, and oligomerization of ethylene to produce 1-octene can be by tetramerization of ethylene. In an embodiment, the process encompasses contacting ethylene with the catalyst composition under ethylene oligomerization conditions effective to produce 1-hexene and/or 1-octene.

The oligomerization of ethylene can be carried out at a pressure of about 0.1 MegaPascals (MPa) to about 20 (MPa), about 1 MPa to about 20 MPa, about 1 MPa to about 10 MPa, about 2 MPa to about 7 MPa, and about 1 MPa to about 5 MPa. Desirably, the oligomerization is at a pressure of about 2 MPa to about 7 MPa.

The oligomerization of ethylene can also be performed at a temperature of about 10 to about 200° C., about 20 to about 100° C., about 30 to about 100° C., about 40 to about 100° C., about 40 to about 80° C., for example, about 40 to about 70° C.

The process can be carried out continuously, semi-continuously or discontinuously.

The process is usually carried out in a reactor. The time it takes for the process to be carried out, usually in the reactor, is also known as residence time. The mean residence time of the process may be from about 10 minutes to about 20 hours, about 20 minutes to about 20 hours, about 1 hour to about 16 hours, about 1 hour to about 8 hours, desirably about 1 to about 4 hours.

For disposal of the catalyst composition (i.e. during operational upset) the catalyst stream can be mixed with the deactivation agent and then transferred as waste. After disposal of the catalyst solution as waste, the associated piping can be flushed by a hydrocarbon solvent for washing purposes.

It was surprisingly found that separate and simultaneous addition of the first pre-catalyst solution and the second pre-catalyst solution directly into the reaction vessel or into a hydrocarbon solvent feed upstream from the reaction vessel eliminates that requirement to premix the solutions in a separate mixing vessel before addition to an oligomerization reactor. Sufficient premixing can be accomplished with the velocity of injection of the first pre-catalyst solution and the second pre-catalyst solution. Residence time before entrance into the oligomerization reactor can be achieved by using a define tube length between injection of the stock solutions into the solvent feed line and the injection into the oligomerization reactor.

The methods disclosed herein include at least the following aspects:

Aspect 1: A method for preparing a homogenous catalyst for use in preparing a linear alpha olefin, comprising: preparing a first pre-catalyst solution by mixing a chromium source and a ligand in a first solvent, wherein the first pre-catalyst solution is stored in a first vessel; preparing a second pre-catalyst solution by mixing an organoaluminum compound and a modifier in a second solvent, wherein the second pre-catalyst solution is stored in a second vessel; and simultaneously feeding the first pre-catalyst solution and the second pre-catalyst solution directly into a reaction vessel, wherein the reaction vessel includes a third solvent.

Aspect 2: A method for preparing a homogenous catalyst for use in preparing a linear alpha olefin, comprising: preparing a first pre-catalyst solution by mixing a chromium source and a ligand in a first solvent, wherein the first pre-catalyst solution is stored in a first vessel; preparing a second pre-catalyst solution by mixing an organoaluminum compound and a modifier in a second solvent, wherein the second pre-catalyst solution is stored in a second vessel; and simultaneously feeding the first pre-catalyst solution and the second pre-catalyst solution directly into a hydrocarbon solvent feed upstream from the reaction vessel.

Aspect 3: The method of Aspect 1 or Aspect 2, wherein the chromium source is selected from organic or inorganic salts, coordinate complexes and organometallic complexes of Cr(II) or Cr(III), preferably $CrCl_3(THF)_3$, CR(III) acetyl acetonate, Cr(III) octanoate, chromium hexacarbonyl, Cr(III)-2-ethylenexanoate, benzene(tricarbonyl)-chromium, Cr(III) chloride, or a combination comprising at least one of the foregoing.

Aspect 4: The method of any of the preceding aspects, wherein the ligand has the general structure $R_1R_2P$—N($R_3$)—P($R_4$)—N($R_5$)—H, wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, aryl and substituted aryl.

Aspect 5: The method of any of the preceding aspects, wherein the modifier is selected from ammonium or phosphonium salts of the type $[H_4E]X$, $[H_3ER]X$, $[H_2ER_2]X$, $[HER_3]X$ or $[ER_4]X$ or HX or RX with E=N or P, X=Cl, Br or I and R=alkyl, cycloalkyl, acyl, aryl, alkenyl, alkynyl or the corresponding bridging di-, tri- or multiunits, or ammonium or phosphonium salts based on cyclic amines, or a combination comprising at least one of the foregoing.

Aspect 6: The method of any of the preceding aspects, wherein the organoaluminum compound includes methylaluminoxane (MAO), trialkyaluminum, or a combination comprising at least one of the foregoing.

Aspect 7: The method of any of the preceding aspects, wherein the first solvent, second solvent, and third solvent independently include an aromatic or aliphatic solvent, or a combination comprising at least one of the foregoing, preferably toluene, benzene, ethylbenzene, cumenene, xylene, mesitylene, hexane, octane, cyclohexane, olefins, such as hexene, heptane, octene, or ethers, such as diethylether or tetrahydrofurane, more preferably an aromatic solvent, most preferably toluene.

Aspect 8: The method of any of the preceding aspects, further comprising removing heat generated from the combination of the organoaluminum compound with the modifier from the reaction vessel.

Aspect 9: The method of any of the preceding aspects, wherein the first vessel, the second vessel, and the reaction vessel are maintained under an inert gas environment.

Aspect 10: The method of any of the preceding aspects, wherein the first pre-catalyst solution in the first vessel is circulated through a first pump and a first cooler, and returned to the first vessel, wherein the first pre-catalyst solution is maintained at a temperature of 0-50° C., preferably, 10-40° C., more preferably 15-35° C.

Aspect 11: The method of Aspect 10, wherein the first vessel is maintained at a pressure of 30 kiloPascals to 8000 kiloPascals, preferably, 50 kiloPascals to 6000 kiloPascals, more preferably, 50 kiloPascals to 3500 kiloPascals.

Aspect 12: The method of any of the preceding aspects, wherein the second pre-catalyst solution from the second vessel is circulated through a second pump and a second cooler, and returned to the second vessel, wherein the second pre-catalyst solution is maintained at a temperature of 0-50° C., preferably, 10-40° C., more preferably 15-35° C.

Aspect 13: The method of Aspect 12, wherein the second vessel is maintained at a pressure of 30 kiloPascals to 8000 kiloPascals, preferably, 50 kiloPascals to 6000 kiloPascals, more preferably, 50 kiloPascals to 3500 kiloPascals.

Aspect 14: The method of any of the preceding aspects, wherein the first pre-catalyst solution is stored in the first vessel for a period of time of 1 hour to 90 days.

Aspect 15: The method of any of the preceding aspects, wherein the second pre-catalyst solution is stored in the second vessel for a period of time of 1 hour to 90 days.

Aspect 16: The method of any of the preceding aspects, wherein a molar ratio of ligand/Cr is 0.5 to 50, preferably 0.8 to 2.0.

Aspect 17: The method of any of the preceding aspects, wherein a molar ratio of Al/Cr is 1.0 to 1000, preferably 10 to 100.

Aspect 18: The method of any of the preceding aspects, wherein a molar ratio of modifier/Cr is 0.1 to 100, preferably 1 to 20.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

Unless otherwise specified herein, any reference to standards, regulations, testing methods and the like, such as ASTM D1003, ASTM D4935, ASTM 1746, FCC part 18, CISPR11, and CISPR 19 refer to the standard, regulation, guidance or method that is in force at the time of filing of the present application.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; C1-6 or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for preparing a homogenous catalyst for use in preparing a linear alpha olefin, comprising:
    preparing a first pre-catalyst solution by mixing a chromium source and a ligand in a first solvent, wherein the first pre-catalyst solution is stored in a first vessel;
    preparing a second pre-catalyst solution by mixing an organoaluminum compound and a modifier in a second solvent, wherein the second pre-catalyst solution is stored in a second vessel; and
    either simultaneously feeding the first pre-catalyst solution and the second pre-catalyst solution directly into a reaction vessel, wherein the reaction vessel includes a third solvent;
    or simultaneously feeding the first pre-catalyst solution and the second pre-catalyst solution directly into a hydrocarbon solvent feed upstream from a reaction vessel.

2. The method of claim 1, wherein the chromium source comprises $CrCl_3(THF)_3$, CR(III) acetyl acetonate, Cr(III) octanoate, chromium hexacarbonyl, Cr(III)-2-ethylenexanoate, benzene(tricarbonyl)-chromium, Cr(III) chloride, or a combination comprising at least one of the foregoing.

3. The method of claim 1, wherein the ligand has the general structure $R_1R_2P—N(R_3)—P(R_4)—N(R_5)—H$, wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, aryl and substituted aryl.

4. The method of claim 1, wherein the modifier is selected from ammonium or phosphonium salts of the type [$H_4E$]X, [$H_3ER$]X, [$H_2ER_2$]X, [$HER_3$]X or [$ER_4$]X or_HX or RX with E=N or P, X=Cl, Br or I and R=alkyl, cycloalkyl, acyl, aryl, alkenyl, alkynyl or the corresponding bridging di-, tri- or multiunits, or ammonium or phosphonium salts based on cyclic amines, or a combination comprising at least one of the foregoing.

5. The method of claim 1, wherein the organoaluminum compound includes methylaluminoxane, trialkylaluminum, or a combination comprising at least one of the foregoing.

6. The method of claim 1, wherein the first solvent, second solvent, and third solvent independently include an aromatic or aliphatic solvent, or a combination comprising at least one of the foregoing.

7. The method of claim 1, further comprising removing heat generated from the combination of the organoaluminum compound with the modifier from the reaction vessel.

8. The method of claim 1, wherein the first vessel, the second vessel, and the reaction vessel are maintained under an inert gas environment.

9. The method of claim 1, wherein the first pre-catalyst solution in the first vessel is circulated through a first pump and a first cooler, and returned to the first vessel, wherein the first pre-catalyst solution is maintained at a temperature of 0-50° C.

10. The method of claim 9, wherein the first vessel is maintained at a pressure of 30 kiloPascals to 8000 kiloPascals.

11. The method of claim 1, wherein the second pre-catalyst solution from the second vessel is circulated through a second pump and a second cooler, and returned to the second vessel, wherein the second pre-catalyst solution is maintained a temperature of 0-50° C.

12. The method of claim 11, wherein the second vessel is maintained at a pressure of 30 kiloPascals to 8000 kiloPascals.

13. The method of claim 1, wherein the first pre-catalyst solution is stored in the first vessel for a period of time of 1 hour to 90 days.

14. The method of, wherein the second pre-catalyst solution is stored in the second vessel for a period of time of 1 hour to 90 days.

15. The method of claim 1, wherein a molar ratio of ligand/Cr is 0.5 to 50, or 0.8 to 2.0.

16. The method of claim 1, wherein a molar ratio of Al/Cr is 1.0 to 1000, or 10 to 100.

17. The method of claim 1, wherein a molar ratio of modifier/Cr is 0.1 to 100, or 1 to 20.

* * * * *